(12) United States Patent
Kim et al.

(10) Patent No.: US 6,989,267 B2
(45) Date of Patent: Jan. 24, 2006

(54) METHODS OF MAKING MICROARRAYS WITH SUBSTRATE SURFACES HAVING COVALENTLY BOUND POLYELECTROLYTE FILMS

(75) Inventors: Namyong Kim, North Andover, MA (US); Athene W. C. Chan, South San Francisco, CA (US); Steven M. Lefkowitz, Branford, CT (US)

(73) Assignee: Agilent Technologies, Inc., Palo Alto, CA (US)

( * ) Notice: Subject to any disclaimer, the term of this patent is extended or adjusted under 35 U.S.C. 154(b) by 511 days.

(21) Appl. No.: 09/900,760

(22) Filed: Jul. 2, 2001

(65) Prior Publication Data

US 2003/0008413 A1 Jan. 9, 2003

(51) Int. Cl.
| | |
|---|---|
| *C12M 1/34* | (2006.01) |
| *C07K 14/00* | (2006.01) |
| *C07K 16/00* | (2006.01) |
| *C07H 21/02* | (2006.01) |
| *C07H 21/04* | (2006.01) |

(52) U.S. Cl. .................. 435/287.2; 530/350; 530/387.1; 536/23.1; 536/24.31; 536/24.33

(58) Field of Classification Search .................. 435/6, 435/7, 287.1, 287.2; 536/23.1, 24.31, 24.33; 530/350, 387.1
See application file for complete search history.

(56) References Cited

U.S. PATENT DOCUMENTS

| | | | |
|---|---|---|---|
| 5,250,613 A | 10/1993 | Bergstrom et al. | |
| 5,629,213 A | 5/1997 | Kornguth et al. | |
| 5,807,522 A | 9/1998 | Brown et al. | |
| 5,858,671 A | * 1/1999 | Jones | ............................ 435/6 |
| 6,110,426 A | 8/2000 | Shalon et al. | |

FOREIGN PATENT DOCUMENTS

| | | |
|---|---|---|
| WO | WO 00/65352 | 11/2000 |

* cited by examiner

*Primary Examiner*—Bradley L. Sisson (57) ABSTRACT

Methods for stably associating a polyelectrolyte coating or film to a substrate surface, as well as the coated substrates produced thereby, are disclosed herein. In the subject methods, substrate surfaces are coated with a polyelectrolyte, and the coated substrate surfaces are treated with a bifunctional molecule under conditions sufficient to stably associate the film to the array surface. The subject methods find use in a variety of different applications, including the production of mircoarrays.

41 Claims, 3 Drawing Sheets

PLLslidesfromSOP

PLLslidesfromSOP/3hourbakingat80C

PLLslidesfrommodifiedSOP/3hourbakingat80C

PLLslidesfrommodifiedSOP/17hourat80C

Figures 4A & 4B

METHODS OF MAKING MICROARRAYS WITH SUBSTRATE SURFACES HAVING COVALENTLY BOUND POLYELECTROLYTE FILMS

BACKGROUND

Biomolecule microarrays are widely used as tools in high throughput technologies, including gene expression analysis, genotyping, nucleic acid analysis, nucleic acid sequencing, mutation analysis, protein and peptide analysis, and screening of potential drugs. Such microarrays are also increasingly used as combinatorial chemistry platforms for drug development and manufacturing.

Microarrays are generally formed on a surface of a glass, metal, plastic, or other substrate, with the substrate surface being functionalized or otherwise rendered capable of binding to biomolecules of interest. The modification of a substrate surface with a thin polyelectrolyte film is a common technique to prepare or treat the surface for subsequent binding of cells, nucleic acids, peptides, proteins, or other biomolecules thereon. The polyelectrolyte, which may be a polyanionic and/or polycationic material, is typically applied to a substrate by dip coating in an aqueous solution of the polyelectrolyte, with the polyelectrolyte binding to the substrate surface via electrostatic interactions. Biomolecules may then be attached to the polyelectrolyte coating via electrostatic interaction, "semi-covalent" or covalent bonding to functional groups on the coating, or other techniques. The polyelectrolyte coating will generally carry a large amount of charge, and may also be treated or passivated chemically prior to use as a research tool.

The use of a polyelectrolyte film in the above manner for anchoring biomolecules to a substrate is attractive due to ease of manufacturing, compatibility with a wide range of glass, metal and metal oxide substrate surfaces, and versatility with respect to a variety of attachable biomolecules. However, the relatively weak interaction between the polyelectrolyte and the underlying substrate surface can result in introduction of defects in a microarray during manufacture and/or use. Particularly, in the case of nucleic acid microarrays, the stresses associated with hybridization of polynucleotide analytes with nucleic acid probes on the array can result in de absorption of the polyelectrolyte from the substrate. Damage from such deabsorption can interfere with hybridization at the damaged portions of the array, cause errors in the optical characterization or readout of the array, or cause other problems that lead to incorrect data or results and which render the microarrays unusable.

There is accordingly a need for a method of securely bonding or stabilizing a polyelectrolyte coating to a substrate surface that provides for easy manufacture of robust, defect-free microarrays of various types of surface displayed entities of interest. The present invention satisfies these needs, as well as others, and generally overcomes the deficiencies found in the background art.

Relevant Literature

U.S. Patents of interest include: U.S. Pat. Nos. 5,250,613; 5,629,213; 5,807,522; and 6,110,426. Also of interest is WO 00/65352. See also: Decher et al., *Current Opinion in Colloid and Interface Science* 1998, 3, 32–39; and Diederich et al., *Advances in Biophysics* 1996, 34, 205–230.

SUMMARY OF THE INVENTION

Methods for stably associating, e.g., covalently bonding, a polyelectrolyte coating or film to a substrate surface, methods for passivating polyelectrolyte coatings and films, and methods of using the same for fabrication of microarrays, are disclosed herein. Also disclosed are microarray devices having polyelectrolyte coatings or films stably associated with a substrate surface, and kits that include the microarray devices. In the subject methods, substrate surfaces are coated with a polyelectrolyte, and the coated substrate surfaces are treated with a bifunctional molecule having a first moiety that covalently bonds to the polyelectrolyte layer, and a second moiety that stably associates with, e.g., covalently bonds to, the substrate surface. The treated substrate surfaces are exposed to a condition or conditions that causes stable association of the film to the surface, e.g., via formation of a covalent bond between the bifunctional molecule and the polyelectrolyte film, and between the bifunctional molecule and the substrate surface. The polyelectrolyte-coated substrates thus formed are usable for fabrication of arrays of biomolecules or other molecules of interest. The polyelectrolyte coated substrates and arrays fabricated therefrom are robust and maintain structural integrity during subsequent uses.

BRIEF DESCRIPTIONS OF THE DRAWINGS

FIG. 3A and FIG. 3B are fluorescent images of cDNA microarrays on glass substrates prepared via prior art techniques, shown after exposure to hybridization conditions FIG. 4A and FIG. 4B are fluorescent images of cDNA microarrays on glass substrates prepared in accordance with the invention, which images illustrate microarray integrity following exposure to hybridization conditions and oven baking.

DEFINITIONS

The term "polymer" means any compound that is made up of two or more monomeric units covalently bonded to each other, where the monomeric units may be the same or different, such that the polymer may be a homopolymer or a heteropolymer. Representative polymers include peptides, polysaccharides, nucleic acids and the like, where the polymers may be naturally occurring or synthetic.

The term "monomer" as used herein refers to a chemical entity that can be covalently linked to one or more other such entities to form an oligomer. Examples of "monomers" include nucleotides, amino acids, saccharides, peptides, and the like. In general, the monomers used in conjunction with the present invention have first and second sites (e.g., C-termini and N-termini, or 5' and 3' sites) suitable for binding to other like monomers by means of standard chemical reactions (e.g., condensation, nucleophilic displacement of a leaving group, or the like), and a diverse element which distinguishes a particular monomer from a different monomer of the same type (e.g., an amino acid side chain, a nucleotide base, etc.). The initial substrate-bound monomer is generally used as a building-block in a multi-step synthesis procedure to form a complete ligand, such as in the synthesis of oligonucleotides, oligopeptides, and the like.

The term "oligomer" is used herein to indicate a chemical entity that contains a plurality of monomers. As used herein, the terms "oligomer" and "polymer" are used interchangeably, as it is generally, although not necessarily, smaller "polymers" that are prepared using the functionalized substrates of the invention, particularly in conjunction with combinatorial chemistry techniques. Examples of oligomers and polymers include polydeoxyribonucleotides, polyribonucleotides, other polynucleotides which are glycosides of a purine or pyrimidine base, polypeptides, polysaccharides, and other chemical entities that contain repeating units of like chemical structure. In the practice of the instant invention, oligomers will generally comprise about 2–50 monomers, preferably about 2–20, more preferably about 3–10 monomers.

The term "ligand" as used herein refers to a moiety that is capable of covalently or otherwise chemically binding a compound of interest. The ligand may be a portion of the compound of interest. Typically, when the present substrates are used in solid phase synthesis, they are used so that "ligands" are synthesized thereon. These solid-supported ligands can then be used in screening or separation processes, or the like, to bind a component of interest in a sample. The term "ligand" in the context of the invention may or may not be an "oligomer" as defined above. The term "ligand" as used herein may also refer to a compound that is synthesized on the substrate surface as well as a compound is "pre-synthesized" or obtained commercially, and then attached to the substrate surface.

The terms "polyelectrolyte" means any polymeric ionic material having a plurality of functional groups capable of holding a positive and/or negative charge, i.e., polycationic and/or polyanionic materials capable of forming salts. "Polyelectrolyte" is used to refer to such polycationic and polyanionic materials in both charged form (i.e. salts) as well as neutralized form. Exemplary polycationic materials include, by way of example, poly(L-lysine), poly(L-glutamine), polyvinylamine, polyethylenimine, other polymeric primary or secondary amines, or copolymers, functionalized derivatives, or blends or combinations thereof, as well as various salts thereof. Exemplary polyanionic materials include, by way of example, polyacrylic acid, poly(L-glutamic acid), poly(L-aspartic acid) and other polycarboxylic acids, polysulfonates, polyphenols, or copolymers, functionalized derivatives, or blends or mixtures thereof, as well as various salts thereof.

The term "passivating group" means any functional group or moiety capable of covalently bonding to a polyelectrolyte film, including bonding to a charged species, or a group capable of carrying a charge, on a polyelectrolyte film.

The term "anchoring group" means any moiety or functional group capable of forming a covalent bond to a group or species on a substrate surface.

The terms "array" and "microarray" mean an arrangement of ligands or molecules of interest on a substrate surface which can be used for analyte detection, combinatorial chemistry, or other applications wherein a two-dimensional arrangement of molecules of interest can be used.

The term "biomolecule" means any organic or biochemical molecule, group or species of interest which may be formed in an array on a substrate surface. Exemplary biomolecules include peptides, proteins, amino acids and nucleic acids.

The term "peptide" as used herein refers to any compound produced by amide formation between a carboxyl group of one amino acid and an amino group of another group.

The term "oligopeptide" as used herein refers to peptides with fewer than about 10 to 20 residues, i.e. amino acid monomeric units.

The term "polypeptide" as used herein refers to peptides with more than 10 to 20 residues.

The term "protein" as used herein refers to polypeptides of specific sequence of more than about 50 residues.

The term "nucleic acid" as used herein means a polymer composed of nucleotides, e.g. deoxyribonucleotides or ribonucleotides, or compounds produced synthetically (e.g. PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions.

The terms "ribonucleic acid" and "RNA"s used herein mean a polymer composed of ribonucleotides.

The terms "deoxyribonucleic acid" and "DNA" as used herein mean a polymer composed of deoxyribonucleotides.

The term "oligonucleotide" as used herein denotes single stranded nucleotide multimers of from about 10 to 100 nucleotides and up to 200 nucleotides in length.

The term "polynucleotide" as used herein refers to single or double stranded polymer composed of nucleotide monomers of generally greater than 100 nucleotides in length.

The terms "reactive site" or "reactive group" refer to moieties that can be used as the starting point in a synthetic organic process. This is contrasted to "inert" hydrophilic groups that could also be present on a substrate surface, e.g, hydrophilic sites associated with polyethylene glycol, a polyamide or the like.

The terms "film" and "coating" mean a layer of polyanionic or polycationic material positioned in association with a surface. The term "layer" thus encompasses both "coating" and "film". Layer thickness may vary, depending upon the particular use of the invention and the type of polyelectrolyte used. It is contemplated, for example, that polyelectrolyte layer thicknesses will generally range in thickness from a monomolecular thickness to about 1 mm, usually from a monomolecular thickness to about 0.1 mm and more usually from a monomolecular thickness to about 500 nm.

The term "sample" as used herein relates to a material or mixture of materials, typically, although not necessarily, in fluid form, containing one or more components of interest.

The term "silanating agent" as used herein means any silane functional group capable of forming an Si—O bond between the silane functional group and a substrate surface.

The terms "nucleoside" and "nucleotide" are intended to include those moieties that contain not only the known purine and pyrimidine bases, but also other heterocyclic bases that have been modified. Such modifications include methylated purines or pyrimidines, acylated purines or pyrimidines, or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like, as well as cycloalkyl groups such as cyclopentyl, cyclohexyl and the like. The term "lower alkyl" intends an alkyl group of 1 to 6 carbon atoms, preferably 1 to 4 carbon atoms.

The term "alkoxy" as used herein refers to a substituent —O—R wherein R is alkyl as defined above. The term "lower alkoxy" refers to such a group wherein R is lower alkyl.

The term "alkylene" as used herein refers to a difunctional saturated branched or unbranched hydrocarbon chain containing from 1 to 24 carbon atoms, and includes, for example, methylene (—$CH_2$—), ethylene (—$CH_2$—$CH_2$—), propylene (—$CH_2$—$CH_2$—$CH_2$—), 2-methylpropylene (—$CH_2$—CH($CH_3$) —$CH_2$—), hexylene (—$(CH_2)_6$—), and the like. "Lower alkylene" refers to an alkylene group of 1 to 6, more preferably 1 to 4, carbon atoms.

The terms "alkenyl" and "olefinic" as used herein refer to a branched or unbranched hydrocarbon group of 2 to 24 carbon atoms containing at least one carbon-carbon double bond, such as ethenyl, n-propenyl, isopropenyl, n-butenyl, isobutenyl, t-butenyl, octenyl, decenyl, tetradecenyl, hexadecenyl, eicosenyl, tetracosenyl and the like.

The terms "halogen," "halo" and "halide" are used in the conventional sense to refer to a chloro, bromo, fluoro or iodo substituent.

As used herein, the term "amino acid" is intended to include not only the L-, D- and nonchiral forms of naturally occurring amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine), but also modified amino acids, amino acid analogs, and other chemical compounds which can be incorporated in conventional oligopeptide synthesis, e.g., 4-nitrophenylalanine, isoglutamic acid, isoglutamine, $\epsilon$-nicotinoyl-lysine, isonipecotic acid, tetrahydroisoquinoleic acid, $\alpha$-aminoisobutyric acid, sarcosine, citrulline, cysteic acid, t-butylglycine, t-butylalanine, phenylglycine, cyclohexylalanine, $\beta$-alanine, 4-aminobutyric acid, and the like.

The terms "protection" and "deprotection" as used herein relate, respectively, to the addition and removal of chemical protecting groups using conventional materials and techniques within the skill of the art and/or described in the pertinent literature; for example, reference may be had to Greene et al., *Protective Groups in Organic Synthesis,* 2nd Ed., New York: John Wiley & Sons, 1991. Protecting groups prevent the site to which they are attached from participating in the chemical reaction to be carried out.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present, and, thus, the description includes structures wherein a non-hydrogen substituent is present and structures wherein a non-hydrogen substituent is not present.

The term "stably associated" when used to refer to the relationship of the polyelectrolyte layer to the substrate surface means that the polyelectrolyte layer is immobilized on the substrate surface under hybridization and washing conditions, e.g., stringent hybridization conditions, as exmplified in the experimental section, infra. As such, the polyelectrolyte layer stably associated to the substrate surface according to the subject invention does not deadsorb from the substrate surface when exposed to stringent hybridization conditions.

An example of "stringent hybridization conditions" is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH 7.6), 5×Denhardt's solution, 10% dextran sulfate, and 20 $\mu$g/ml denatured, sheared salmon sperm DNA, followed by washing the filters in 0.1×SSC at about 65° C. Stringent hybridization conditions are hybridization conditions that are at least as stringent as the above representative conditions. Other stringent hybridization conditions are known in the art and may also be employed to identify nucleic acids of this particular embodiment of the invention.

DETAILED DESCRIPTION OF THE INVENTION

Disclosed herein are methods for stably associating, e.g., covalently bonding, a polyelectrolyte coating or film to a substrate surface, methods for passivating polyelectrolyte coatings and films, and methods of using the same for fabrication of biomolecule microarrays. The subject methods provide improved adhesion and stability of polyelectrolyte films on substrate surfaces for the production of high performance microarrays of biomolecules. The methods of the invention are relatively simple and inexpensive, and may be carried out prior to or after attachment of biomolecules to the substrate surface. The inventive methods may be implemented with minimal change in current array production processes.

The subject methods include, in general terms, coating a substrate surface with a polyelectrolyte layer, and stably associating, e.g., covalently bonding, the polyelectrolyte layer to the substrate surface. More specifically, the method includes treating or contacting the polyelectrolyte-coated substrate surface with a bifunctional molecule having a first moiety that passivates, e.g., by covalently bonding to, the polyelectrolyte layer, and a second moiety that stably associates with, e.g., covalently bonds to, the substrate surface. By "stably associates with" is meant that the film is immobilized on the substrate surface during standard hybridization, washing and visualization conditions, where the film does not deadsorb from the substrate surface under these conditions. In many embodiments, the bifunctional molecule, in other words, is an agent or reactant having at least one functional group capable of covalently bonding to the polyelectrolyte coating and at least one functional group capable of covalently bonding to the substrate surface itself. The method also comprises subjecting the substrate and polyelectrolyte layer to a condition or conditions suitable to effect covalent bonding of the bifunctional molecule to the polyelectrolyte film and to the substrate surface. The functional group or moiety bonding to the polyelectrolyte may comprise a passivating group that reacts with a charged species, or a group capable of carrying a charge, on the polyelectrolyte. The agent may include one or more additional functional groups capable of bonding to a ligand or other molecule of interest.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a", "and" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit, unless the context clearly dictates otherwise, between the upper and lower limit of that range and any other stated or intervening value in that stated range, is encompassed within the invention. The upper and lower limits of these smaller ranges may, independently, be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As noted above, the invention provides methods for stably associating a polyelectrolyte layer with a substrate surface and methods of using the same for fabrication of biomolecule microarrays. The methods of the invention comprise coating a substrate surface with a layer of polyelectrolyte, and then stably associating, e.g., covalently bonding, the polyelectrolyte layer to the substrate surface. In many embodiments, the stable association step includes contacting the polyelectrolyte-coated substrate surface with an agent having a first functional group capable of passivating, and often covalently bonding to, the polyelectrolyte layer, and a second functional group capable of stably associating with, e.g., covalently bonding to, the substrate surface itself. The second functional group may reach the substrate surface through pores, openings or defects present in the polyelectrolyte layer that have dimensions such that the second functional group can contact, e.g., and bond to, the substrate. The methods additionally include exposing the polyelectrolyte-coated substrate and agent to a condition or conditions that cause the film to become stably associated with the substrate surface, e.g., that cause the first functional group to covalently bond to the polelectrolyte layer, and the second functional group to covalently bond to the substrate surface. The functional group bonding to the polyelectrolyte layer may, in certain embodiments, comprise a group that passivates a charged species, or a group capable of carrying a charge, on a neutralized polyelectrolyte layer.

Substrates

A variety of substrates may be used with the invention for the fabrication of different types of microarrays, and the size and shape of the substrate and substrate surfaces, and the substrate material, will necessarily vary according to the particular use of the invention. Substrates may be flexible or rigid. By flexible is meant that the support is capable of being bent, folded or similarly manipulated without breakage. Examples of solid materials which are flexible solid supports with respect to the present invention include membranes, flexible plastic films, and the like. By rigid is meant that the support does not readily bend, i.e. the support is inflexible. Both flexible and rigid substrates must provide physical support and structure for microarray fabrication thereon, and not interfere with detection hybridization results using the microarrays.

The substrates may take a variety of configurations ranging from simple to complex. Thus, the substrate could have an overall slide or plate configuration, such as a rectangular, square or disc configuration. In many embodiments, such as those wherein arrays of nucleic acid probe spots are formed on a substrate surface, the substrate will have a rectangular cross-sectional shape, having a length of from about 4 mm to 200 mm, usually from about 4 to 150 mm and more usually from about 4 to 125 mm and a width of from about 4 mm to 200 mm, usually from about 4 mm to 120 mm and more usually from about 4 mm to 80 mm, and a thickness of from about 0.01 mm to 5.0 mm, usually from about 0.1 mm to 2 mm and more usually from about 0.2 to 1 mm. The above dimensions are, of course, exemplary only and may vary as required.

The substrates may be fabricated from a variety of materials. In certain embodiments, e.g. for the fabrication of nucleic acid microarrays for use in research, the materials from which the substrate may be fabricated should ideally exhibit a low level of non-specific binding during hybridization events. In many situations, it will also be preferable to employ a material that is transparent to visible and/or UV light. For flexible substrates, materials of interest include, for example, nylon, nitrocellulose, polypropylene, polyester films, such as polyethylene terephthalate, polymethyl methacrylate or other acrylics, polyvinyl chloride or other vinyl resin, and the like. Various plasticizers and modifiers may be used with polymeric substrate materials to achieve selected flexibility characteristics. For rigid substrates, specific materials of interest include: silicon; glass; rigid plastics, e.g. polytetrafluoroethylene, polypropylene, polystyrene, polycarbonate, and blends thereof, and the like; metals, e.g. gold, platinum, and the like; etc. In certain embodiments transparent substrate materials are desirable to allow easy optical detection of hybdridization events associated with a microarray on the substrate surface.

The substrate surface should be smooth or substantially planar, or have periodic irregularities, i.e. a series of depressions forming wells, such as depressions or elevations, or have a porous surface, such as is found in porous glass or silica. The surface may be modified with one or more different layers of compounds, prior to depositing the polyelectrolyte layer on the surface. Such surface modification serves to modify the properties of the surface in a desirable manner. Such modification layers, when present, will generally range in thickness from a monomolecular thickness to about 5 microns, usually from a monomolecular thickness to about 500 nm and more usually from a monomolecular thickness to about 100 nm. Modification layers of interest include: inorganic and organic layers such as metals, metal oxides, conformal silica or glass coatings, polymers, diamond-like carbon, small organic molecules and the like. Polymeric layers may include, for example, polysaccharides, phospholipids, polyurethanes, polyesters, polycarbonates, polyureas, polyamides, polyarylene sulfides, polysiloxanes, polyimides, polyacetates, and the like, as well as copolymers and blends thereof. Inorganic coating layers may comprise, for example, silica, alumina or other metal oxide, aluminum nitride or other metal nitride, aluminum carbide or other metal carbide, or gold, silver or other metal or metal alloy.

The substrate surface will have at least a monolayer of species thereon which are capable of forming a covalent bond to an overlying polyelectrolyte layer in accordance with the invention. In this regard, the substrate surface may be modified or functionalized by chemical treatment to alter its properties and functionality to accommodate a specific moiety or functional group. For example, a polymeric substrate surface may be subject to ozonolysis to introduce carbonyl and hydroxyl functional groups thereon. Such carbonyl and hydroxyl groups may be subject to further treatment to provide different functional groups. Inorganic and polymeric substrates may be subject to acid treatment, treatment with base, subject to fluorine gas, or exposed to other reactive gas or solution, in order to change substrate surface properties and functionality.

Polyelectrolyte Layer

The polyelectrolyte layer coated on the substrate surface will necessarily vary in composition and thickness according to the particular use of the invention. The polyelectrolyte layer may be formed by dip coating, spin coating, spray coating, or other coating technique wherein a solution or suspension of the polyelectrolyte is deposited on the substrate surface, followed by drying via vacuum, forced air oven, convection oven, or other drying technique to remove solvent or carrier and leave a polyelectrolyte layer on the substrate. The polyelectrolyte coating may also be formed on the substrate surface by Langmuir-Blodgett deposition, or transfer of a free-standing polyelectrolyte film to the substrate surface. Polyelectrolyte layer thickness may vary, depending upon the particular use of the invention and the type of polyelectrolyte used. Polyelectrolyte layer thicknesses may range in thickness from a monomolecular thickness to 5 microns, usually from a monomolecular thickness to about 500 nm and more usually from a monomolecular thickness to about 100 nm.

The polyelectrolyte material may be a polycationic or polyanionic material, and may be deposited on the substrate surface in both charged form (i.e., as a polymeric salt), as well as neutralized form. Polycationic materials usable with the invention include, for example, poly(L-lysine), poly(L-glutamine), polyvinylamine, polyethylenimine, other polymeric primary or secondary amines, or copolymers, functionalized derivatives, or blends or combinations thereof, as well as various salts thereof. Exemplary polyanionic materials include, by way of example, polyacrylic acid, poly(L-glutamic acid), poly(L-aspartic acid) and other polycarboxylic acids, polysulfonates, polyphenols, or copolymers, functionalized derivatives, or blends or mixtures thereof, as well as various salts thereof.

While the invention herein is mainly described in terms of polyelectrolyte layers, in certain embodiments, the layer is not a polyelectrolyte layer, but a non-polyelectrolyte polymeric layer. As such, the methods of the subject invention are applicable to the stable association of a non-polyelectrolyte layer to a substrate surface, e.g., via use of a bifunctional molecule.

Bifunctional Molecule for Covalently Bonding the Polyelectrolyte Layer to the Substrate Surface As noted above, a bifunctional molecule or agent is used which includes a first moiety or functional group capable of covalently bonding to the polyelectrolyte layer, and a second moiety or functional group capable of covalently bonding to the substrate surface, such that the polyelectrolyte layer is covalently bonded to the substrate surface through the agent. The first functional group may bond directly to a charge bearing group, or group capable of bearing a charge, and in this regard the first functional group can be referred to as a "passivating group". The second functional group, for reason of clarity, is hereinafter referred to as an "anchoring group". The passivating group may comprise any functional group or moiety capable of covalently bonding to a polyelectrolyte film, including bonding to a charged species, or a group capable of carrying a charge, on a polyelectrolyte film. The anchoring group may comprise any moiety or functional group capable of forming a covalent bond to a group or species on a substrate surface.

A variety of passivating groups and anchoring groups are contemplated, depending upon the nature of the polyelectrolyte layer and substrate surface utilized. For example, where the polyelectrolyte comprises a polyamine such as poly(L-lysine) or poly(L-arginine). The passivating group may comprise an anhydride, an acid chloride, ester, alkyl halides, chlorocarbonate, chloroformate, thiocyanate, isocyanate, carbonyl compounds, or other functional group capable of reacting with an amine on the polyelectrolyte to form an amide. In the case of polycarboxylic acid and polysulfonic acid polyelectrolytes, the passivating group may comprise a group capable of forming a carboxylic ester or a sulfonate ester respectively. The chemistry associated with passivation of polyelectrolytes is well known, and numerous passivating groups for the aforementioned polyelectrolytes will suggest themselves to those skilled in the art upon review of the present disclosure.

Likewise, a variety of anchoring groups may be used with the invention. In the case of glass and silicate substrates or glass and silicate-coated substrates, the anchoring group may comprise a silanating group such as a mono-, di- or tri-alkoxysilyl ether capable of reacting with a Si(OH) group on the substrate surface to form an Si—O bond with the substrate surface. Various metal alkoxide or carboxylate groups may be used as anchoring groups for corresponding metal oxide substrate surfaces. Sulfides, selenides and other compounds may be used as the anchor groups on coinage metal (Au, Ag, Cu, Pd . . . ) surfaces.

Where the substrate is a polymeric material, the anchoring group may comprise a functional group capable of covalently bonding to a functional group present in the polymeric substrate material. For example, polystyrene, polyacrylic and vinyl substrates may be formed with a percentage of di-functional monomers such that a residual amount of unsaturated, reactive acrylic, styryl or vinyl groups remain in the polymeric substrate and are exposed on surfaces of the substrate. In this case, the anchoring group may comprise an acrylic, styryl or vinyl group, or like reactive unsaturated group, that is capable or reacting with and covalently bonding to the residual unsaturated groups on the substrate surface. Covalent bonding between a reactive unsaturated anchor group and a residual unsaturated group on a substrate surface can be effected by UV treatment or curing. The anchor group may also comprise an epoxy group capable of reacting with amino or hydroxyl groups present on a polymeric substrate.

The bifunctional molecule comprising the passivating group and anchoring group may also comprise a separating group or chain of varying length. For example, in certain embodiments the passivating and anchoring groups may be closely positioned on the same molecule, while in other embodiments the passivating group and anchoring group may be substantially separated by a flexible or rigid (or both) portion of molecule.

The bifunctional molecule may be applied to the polyelectrolyte-coated surface by contacting a solution of the bifunctional molecule to the polyelectrolyte-coated surface by dipping, spraying or other exposure technique. In cases where the bifunctional molecule is a liquid, the bifunctional molecule may be applied neat to the polyelectrolyte-coated surface. The amount of bifunctional molecule that is applied to the film varies depending on the intended use of the product. Where one desires to preserve some reactive groups for subsequent reaction with other molecules, e.g., ligands, such as in the production of microarrays in which the ligand is deposited following the bifunctional group, the amount of bifunctional molecules that is deposited will generally be chosen so that not all reactive groups are reacted. In alternative embodiments, the amount of bifunctional molecule applied to the polyelectrolyte surface should be such that the number of passivating groups is stoichiometrically equal to, or in slight stoichiometric excess of, the potential reaction sites on the polyelectrolyte layer, and such that the number of anchoring groups is stoichiometrically equal to, or in slight stoichiometric excess of, the potential reaction sites for the anchoring groups on the substrate surface. In this manner, all or substantially all of the bifunctional molecules may each have a passivating group that is covalently bonded to the polyelectrolyte layer, and an anchoring group that is covalently bonded to the substrate surface, to provide optimum adhesion of the polyelectrolyte layer to the substrate surface. Large stoichiometric excesses of either the passivating group or the anchoring group or both may, in certain instances, result in non-optimal bonding between the polyelectrolyte layer and the substrate surface due to the presence of bifunctional molecules which are covalently bound only to the polyelectrolyte layer or the substrate surface, but not both.

The substrate layer and polyelectrolyte layer with bifunctional molecules contacted thereon ideally will be subjected to a condition or conditions which facilitate the formation of a covalent bond between the anchoring group and the polyelectrolyte layer, and between the anchoring group and the substrate surface. Such conditions will necessarily vary depending upon the nature of passivating and anchoring groups, the polyelectrolyte material, and the nature of the substrate surface. Conditions usable to effect the desired covalent bonding may comprise, for example, exposure to heating, e.g., from temperatures ranging from about 20° C. to 120° C., usually from about 30° C. to 100° C. and more usually from about 50° C. to 80° C., pH adjustment or buffering, the presence of catalytic agents which facilitate formation of the desired covalent bonding, the providing of a suitable duration for the contacting of the bifunctional molecule with the polyelectrolyte layer and substrate surface (where the incubation time typically ranges from about 0 to 24 hour, usually from about 1 to 20 hour and more usually from about 2 to 17 hour), or any other condition which will facilitate the covalent bonding of the passivating group to the polyelectrolyte layer and the covalent bonding of the anchoring group to the substrate layer.

Methods

Figure 1A:
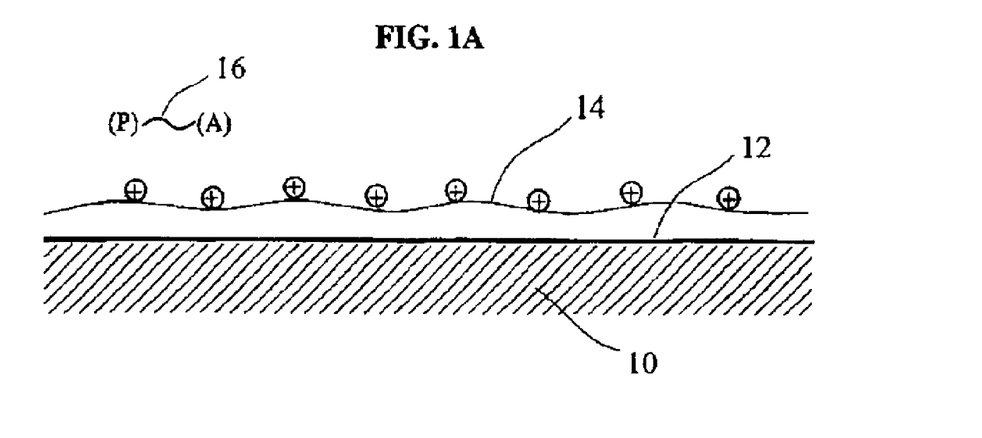
FIG. 1A through FIG. 1C schematically illustrate a method for bonding a polyelectrolyte coating to a substrate surface in accordance with the present invention.
Figure 1B:
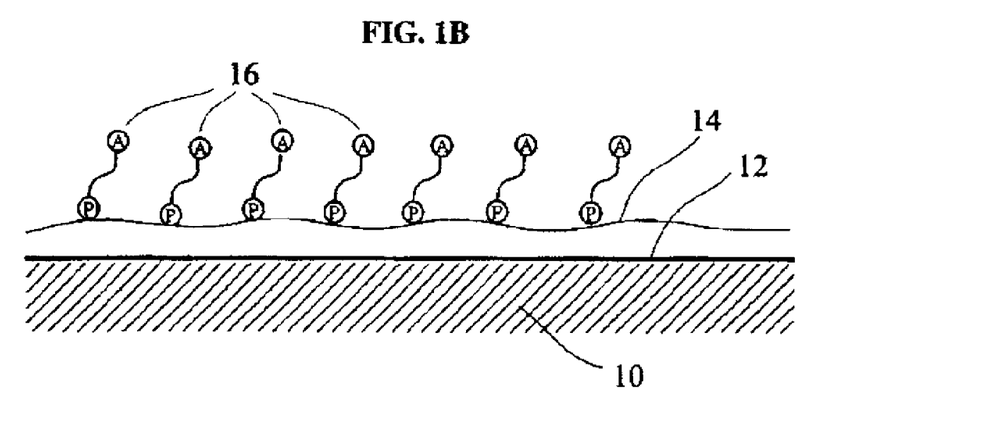
Figure 1C:
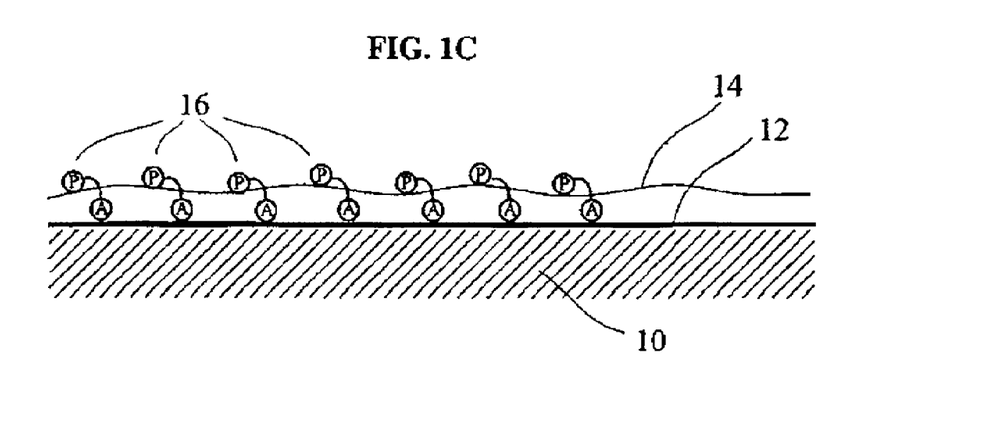

With the above in mind, reference is now made to FIG. 1A through FIG. 1C, wherein a method in accordance with the invention is illustrated schematically. In FIG. 1A there is shown a substrate 10 having a surface 12 that is suitable for formation of an array of biomolecules (not shown). Substrate 10 may be made of one of the materials discussed above, and configured in the manner discussed above.

A layer 14 of polyelectrolyte material is positioned on substrate surface 12. As shown in FIG. 1A, the polyelectrolyte is a polycationic material, and a plurality of positive (+) charges are shown in association with the layer 14. The polycationic material may comprise poly(L-lysine) as noted above, which is commonly used in fabrication of nucleic acid microarrays, with the positive charges (+) being due to the protonated amino groups ($NH_3^+$) present in poly(L-lysine).

FIG. 1B shows the substrate 10 and polyelectrolyte layer 14 after being contacted with agents or reactants 16 in accordance with the invention. Agents 16 are bifunctional molecules having a first functional group, shown as passivating group (P), capable of forming a covalent bond to a group on polyelectrolyte layer 14, and a second functional group, shown as anchoring group (A) capable of forming a covalent bond to a group on substrate surface 12. Passivating group (P) may comprise one of the various functional groups discussed above. In the case where polyelectrolyte layer 14 comprises poly(L-lysine) or other polyamine, the passivating group (P) may comprise an anhydride or cyclic anhydride that is capable of reacting with the amino groups to form amide bonds, as described further below. The anchoring group (A) may comprise one of the functional groups discussed above that will form a covalent bond with species present on substrate surface 12, either directly or when subsequently exposed to an immobilizing condition or conditions which cause the groups (A) to react with and covalently bond to substrate surface 12. In the case of glass or $SiO_2$ substrates (or in cases wherein substrate surface 12 has been coated with $SiO_2$), the anchoring group (A) may comprise a trialkoxysilyl group which, upon subsequent exposure to an anchoring condition such as heating or baking, will link or attach the agents 16 covalently to substrate surface 12 through anchoring group (A), as shown in FIG. 1C.

Figure 2A:
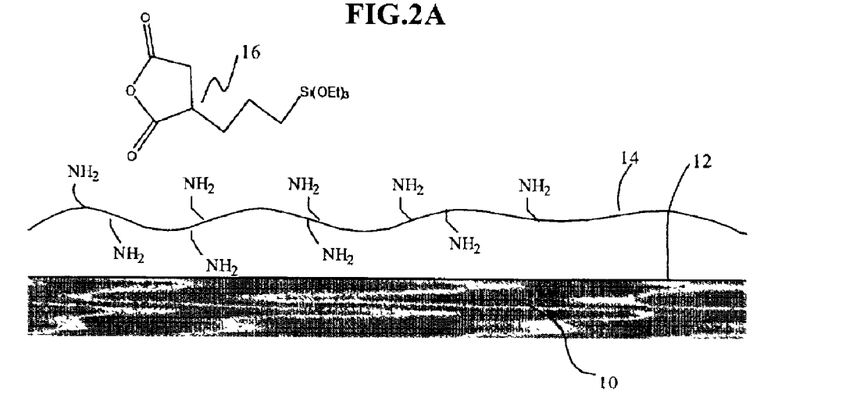
FIG. 2A through FIG. 2C schematically illustrate a specific embodiment of a method for bonding a polyelectrolyte coating to a substrate surface using triethoxysilylpropylsuccinic anhydride.
Figure 2B:
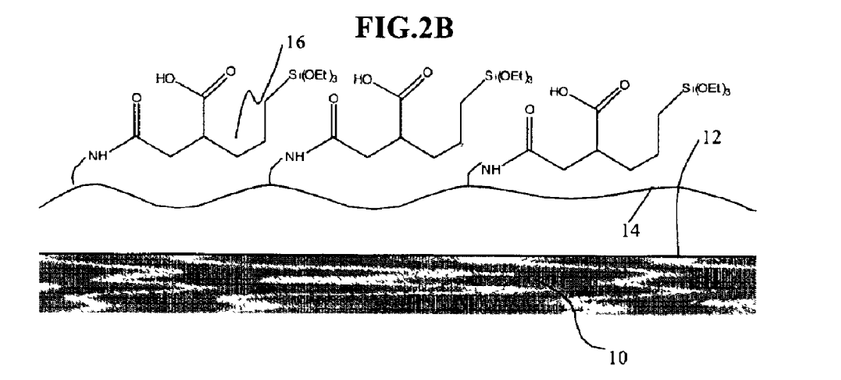
Figure 2C:
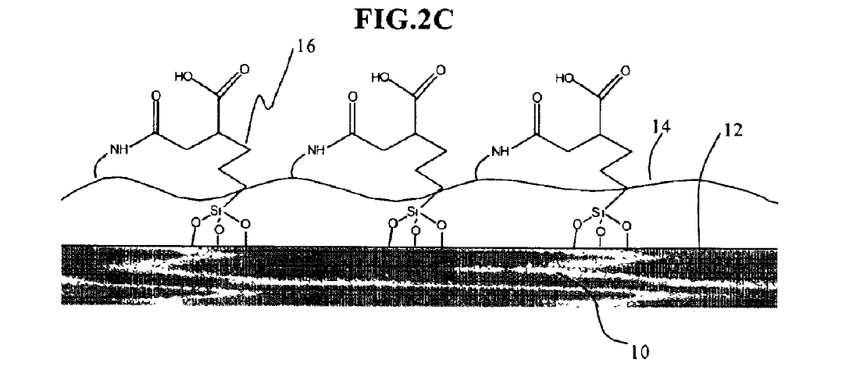

Referring now to FIG. 2A through FIG. 2C, a specific embodiment of a method in accordance with the invention is shown schematically, wherein like reference numbers are used to denote like parts. FIG. 2A shows a substrate 10 having a surface 12 that is suitable for formation of an array of biomolecules thereon. As noted above, substrate 10 may comprise a glass slide or other suitable substrate. In the embodiment of FIG. 2A through FIG. 2C, substrate surface 12 comprises $SiO_2$. A layer 14 of polyelectrolyte material in the form of a polyamine such as poly(L-lysine) is located adjacent substrate surface 12. The polyamine of layer 14 is shown in neutralized form, i.e., with a plurality of unprotonated amine groups.

In the method of the invention, the polyamine layer is treated or contacted with a bifunctional agent or reactant 16 having a first, passivating group capable of covalently bonding to layer 14 of polyamine, and a second, anchoring group capable of covalently bonding to substrate surface 12. In this embodiment, a tri-alkoxysilyl cyclic anhydride is used as a bifunctional agent 16, with the anhydride portion serving as a passivating group, and the trialkoxysilyl portion serving as an anchoring group:

19 wherein n is either zero or an integer from 1 to 10, m is either zero or an integer from 1 to 10, and R is any alkyl group, alkenyl group, or alkalene group terminated with a functional group such as an alkoxy or halide. The values of the integers m and n can be varied to control the spacing between the passivating group and anchoring group as desired. The value for n may, in specific embodiments, equal one or two, while m may have a value within the range of from zero to four. In the following Examples, the trialkoxysilyl cyclic anhydride agent 16 used is triethoxypropyl succinic anhydride wherein n=1 and m=3. The values of the integers m and n, as well as the nature of the R group, may be varied to tailor the solubility of bifunctional molecule 16 in desired solvents or to control the reactions required for formation of the desired covalent bonds. The succinic anhydride portion or moiety provides a functional group capable of covalently bonding to and passivating the layer 14 of polyamine, and the triethoxysilyl group is capable of covalently bonding to substrate surface 12.

As shown in FIG. 2B, the succinic anhydride portion of agent 16 reacts with an amine group of layer 14 via a ring opening reaction to form an amide linkage between agent 16 and layer 14. The reaction of the succinic anhydride portion of agent 16 with an amine group on layer 14 also serves to passivate layer 14 by effectively converting the amine group to an un-protonatable species.

The triethoxysilyl group of agent 16, as shown in FIG. 2C, covalently bonds to the silicate substrate surface 12 upon heating by reacting with oxygen atoms, which may be present in the form of SiOH groups, on the silicate surface 12. The reaction forms three Si—O bonds between agent 16 and surface 12 and results in condensation of three ethanol molecules. The reaction of the triethoxysilyl groups with substrate surface 12 can be achieved by baking the substrate 10 and layer 14. The Si—O bonds serve to covalently bond or attach agent 16 to surface 12. Thus, agents 16 each are bonded to layer 14 of polyelectrolyte via an amide linkage, and to substrate surface 16 via three Si—O bonds, such that layer 14 is securely, covalently bonded to surface 12 to provide a robust platform for a biomolecule microarray that will be resistant to deformation during subsequent use.

Microarray Fabrication

Also provided by the subject invention are microarrays and methods of fabricating microarrays of a variety of ligands. In the broadest sense, the arrays of the subject invention are arrays of polymeric binding agents, where the polymeric binding agents may be any of: peptides, proteins, nucleic acids, polysaccharides, synthetic mimetics of such biopolymeric binding agents, etc. In many embodiments of interest, the arrays are arrays of nucleic acids, including oligonucleotides, polynucleotides, cDNAs, mRNAs, synthetic mimetics thereof, and the like. Where the polymeric compounds are nucleic acids, the nucleic acids will generally be at least about 5 nt, usually at least about 10 nt and more usually at least about 15 nt in length, where the nucleic acids may be as long as 5000 nt or longer, but generally will not exceed about 3000 nt in length and usually will not exceed about 2000 nt in length.

The subject arrays include at least two distinct polymeric ligands that differ by monomeric sequence immobilized on, e.g., covalently attached to, different and known locations on the substrate surface. Each distinct polymeric ligand sequence of the array may be present as a composition of multiple copies of the polymer on the substrate surface, e.g. as a spot on the surface of the substrate. The number of distinct polymeric ligand sequences, and hence spots or similar structures, present on the array may vary, but is generally at least 2, usually at least 5 and more usually at least 10, where the number of different spots on the array may be as a high as 50, 100, 500, 1000, 10,000 or higher, depending on the intended use of the array. The spots of distinct polymeric ligands present on the array surface are generally present as a pattern, where the pattern may be in the form of organized rows and columns of spots, e.g. a grid of spots, across the substrate surface, a series of curvilinear rows across the substrate surface, e.g. a series of concentric circles or semi-circles of spots, and the like. The density of spots present on the array surface may vary, but will generally be at least about 10 and usually at least about 100 spots/cm$^2$, where the density may be as high as $10^6$ or higher, but will generally not exceed about $10^5$ spots/cm$^2$.

To prepare the subject arrays, at least two distinct polymers are contacted with the substrate surface having a polyelectrolyte layer present thereon. By distinct is meant that the two polymers differ from each other in terms of sequence of monomeric units. The number of different polymers that are contacted with the substrate surface may vary depending on the desired nature of the array of the to be produced, i.e. the desired density of polymeric structures. Generally, the number of distinct polymers that are contacted with the surface of the array will be at least about 5, usually at least about 10 and more usually at least about 100, where the number may be as high as 1,000,000 or higher, but in many embodiments will not exceed about 500,000 and in certain embodiments will not exceed about 100,000. The polymers are generally contacted with the surface in an aqueous solvent, such that aqueous conditions are established at the surface location to which the polymer is to be covalently attached. Each polymer is typically contacted with the substrate surface as part of an aqueous composition, i.e. an aqueous composition of the polymer in an aqueous solvent is contacted with the surface of the array.

The aqueous solvent may be either water alone or water in combination with a co-solvent, e.g. an organic solvent, and the like. The aqueous composition may also contain one or more additional agents, including: acetic acid, monochloro acetic acid, dichloro acetic acid, trichloro acetic acid, acetonitrile, catalysts, e.g. lanthanide (III) trifluoromethylsulfate, lithium chloride, buffering agents, e.g. sodium phosphate, salts, metal cations, surfactants, enzymes, etc.

The aqueous polymer composition may be contacted with the surface using any convenient protocol. Generally, the aqueous polymer composition is contacted with the surface by depositing the aqueous polymer composition on the surface of the substrate. The aqueous volume may be deposited manually, e.g. via pipette, or through the use of an automated machine or device. A number of devices and protocols have been developed for depositing aqueous solutions onto precise locations of a support surface and may be employed in the present methods. Such devices include "ink-jet" printing devices, mechanical deposition or pipetting devices and the like. See e.g. U.S. Pat. Nos. 4,877,745; 5,338,688; 5,474,796; 5,449,754; 5,658,802; 5,700,637; and 5,807,552; the disclosures of which are herein incorporated by reference. Robotic devices for precisely depositing aqueous volumes onto discrete locations of a support surface, i.e. arrayers, are also commercially available from a number of vendors, including: Genetic Microsystems; Cartesian Technologies; Beecher Instruments; Genomic Solutions; and BioRobotics. For example, the ligands may be prepared and then transferred to a multi-well plate, incubated, and loaded onto the surface of a polyelectrolyte-coated substrate using a robotic multi-pin tool such as a Biomek robot. The ligands are typically deposited in an array of spots as noted above. The particular patterning of the array may vary depending upon its desired use.

The resultant ligands are then immobilized on the polyelectrolyte layer. For example, where the ligands are nucleic acids, the nucleic acid spots may be cross-linked with irradiation using an irradiation cross-linker such as Stratalinker (Stratagene), then washed and dried. Various methods for production of nucleic acid arrays in the above manner are known to those of skill in the art and are disclosed in U.S. Pat. Nos. 6,110,426, 6,087,102, 6,004, 755, 5,445,934; 5,532,128; 5,556,752; 5,242,974; 5,384,261; 5,405,783; 5,412,087; 5,424,186; 5,429,807; 5,436,327; 5,472,672; 5,527,681; 5,529,756; 5,545,531; 5,554,501; 5,561,071; 5,571,639; 5,593,839; 5,599,695; 5,624,711; 5,658,734; and 5,700,637; the disclosures of which are herein incorporated by reference.

After depositing, cross-linking and drying the ligand, e.g., nucleic acid spots, the polyelectrolyte layer and substrate surface is treated with the bifunctional agent described above. The passivating groups present in the agent covalently bond to and passivate groups on the polyelectrolyte layer, and covalently bond to groups on the substrate surface.

Utility

The substrate surfaces produced in accordance with the invention find use in a variety microarray applications, such as microarrays of nucleic acids, including oligonucleotides and polynucleotide of ribonucleic and deoxyribonucleic acids, microarrays of amino acids, peptides and proteins. More specifically, the invention provides methods for making robust, stable microarrays for analyte detection applications in which the presence of a particular analyte in a given sample may be detected. Protocols for carrying out such assays are well known to those of skill in the art and need not be described in detail herein. Briefly, a sample comprising the analyte of interest is contacted with an array produced according to the subject methods under conditions sufficient for the analyte to bind to its respective binding pair member that is present on the array. Thus, if the analyte of interest is present in the sample, it binds to the array at the site of its complementary binding member and a complex is formed on the array surface. The presence of this binding complex on the array surface is then detected, e.g. through use of a signal production system, e.g. an isotopic or fluorescent label present on the analyte, etc. The presence of the analyte in the sample is then deduced from the detection of binding complexes on the substrate surface.

Specific analyte detection applications of interest include hybridization assays in which the nucleic acid arrays of the subject invention are employed. In these assays, a sample of target nucleic acids is first prepared, where preparation may include labeling of the target nucleic acids with a label, e.g. a member of signal producing system. Following sample preparation, the sample is contacted with the array under hybridization conditions, whereby complexes are formed between target nucleic acids that are complementary to probe sequences attached to the array surface. The presence of hybridized complexes is then detected. Specific hybridization assays of interest which may be practiced using the subject arrays include: gene discovery assays, differential gene expression analysis assays; nucleic acid sequencing assays, and the like. Patents and patent applications describing methods of using arrays in various applications include: U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; WO 95/21265; WO 96/31622; WO 97/10365; WO 97/27317; EP 373 203; and EP 785 280; the disclosures of which are herein incorporated by reference.

In gene expression analysis with microarrays, an array of "probe" nucleic acids is contacted with a nucleic acid sample of interest. Contact is carried out under hybridization conditions and unbound nucleic acid is then removed. The resultant pattern of hybridized nucleic acid provides information regarding the genetic profile of the sample tested. Gene expression analysis finds use in a variety of applications, including: the identification of novel expression of genes, the correlation of gene expression to a particular phenotype, screening for disease predisposition, identifying the effect of a particular agent on cellular gene expression, such as in toxicity testing; among other applications.

In certain embodiments, the subject methods include a step of transmitting data from at least one of the detecting and deriving steps, as described above, to a remote location. By "remote location" is meant a location other than the location at which the array is present and hybridization occur. For example, a remote location could be another location (e.g. office, lab, etc.) in the same city, another location in a different city, another location in a different state, another location in a different country, etc. The data may be transmitted to the remote location for further evaluation and/or use. Any convenient telecommunications means may be employed for transmitting the data, e.g., facsimile, modem, internet, etc.

The covalent bonding of the polyelectrolyte layer to the substrate surface as provided by the invention prevents deadsorption or deformation of the polyelectrolyte layer which could otherwise occur during hybridization or other reaction with the nucleic acid spots on the polyelectrolyte layer.

Kits

The invention also provides kits for use in fabrication of polyelectrolyte-coated substrates and microarrays. The subject kits may comprise, for example, one or more substrates having a polyelectrolyte-coated surface, and a solution of bifunctional agent or reactant having a passivating group and an anchoring group thereon which are respectively capable of covalently bonding to the polyelectrolyte layer and the substrate surface. For example, poly(L-lysine)-coated glass slides are commercially available from Aldrich-Sigma of Saint Louis, Mo., and a kit in accordance with the invention may comprise a plurality of such coated slides, vials or containers of predetermined volumes of suitably buffered solution of bifunctional molecule for each coated slide, and instructions for application of the solution of bifunctional molecule to the coated slides and the conditions needed to effect covalent bonding of the bifunctional molecules to the coating and the slide surface.

In other embodiments, the subject kits may comprise one or more uncoated substrates together with vials or containers of predetermined volumes of solution of polyelectrolyte suitable for use in forming a layer of polyelectrolyte on surfaces of the substrates, vials or containers of predetermined volumes of suitably buffered solution of bifunctional molecule for use with the substrates after the coating thereof with polyelectrolyte, and suitable instructions for use of the aforementioned items in the kit. The instructions may be present on at least one of a package insert and the package of the kit.

In still other embodiments, the subject kits may comprise substrates with polyelectrolyte layers coated thereon wherein the polyelectrolyte layer has been covalently bound to the substrate surface in accordance with the invention. The kit may include suitable reagents for forming microarrays of nucleic acids or other molecules of interest on the polyelectrolyte-coated substrate surfaces.

In other embodiments, the polyelectrolyte-coated substrate surface may include an array of molecules of interest, such as an array of nucleic acids, already formed on the coated substrate surfaces. That is, the coated substrates are in microarray form. The kits may further include one or more additional components necessary for carrying out the analyte detection assay, such as sample preparation reagents, buffers, labels, reagents for generating a labeled target nucleic acid sample, and the like. In addition, the kits typically further include instructions for how practice the subject analyte detection methods according to the subject invention, where these instructions are generally present on at least one of a package insert and the package of the kit.

Experimental

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXAMPLE 1

Poly(L-lysine)-Coated Substrate

The Poly-L-Lysine Solution used in this example was purchased from Sigma Dianostics Inc. (Cat # P8920) and used as received. The glass slides were placed in 5% RBS solution, and were sonicated for approximately 15 minutes. They were then rinsed with running deionized water for approximately 5 minutes. The glass slides were transferred directly to a concentrated wash solution for approximately 15 minutes. They were then rinsed with running deionized water for approximately 10 minutes. The Poly-L-Lysine coating solution was prepared by adding 80 mL 0.1% w/v Poly-L-Lysine solution and 80 mL 1×PBS to 640 mL milli-Q water. The coating solution was made fresh before use and was stirred on a stir plate at room temperature. The slides were dripped briefly and were put into the Poly-L-Lysine coating solution for approximately 20 minutes, with gentle agitation. The slides were then rinsed with running DI water for approximately 5 minutes. The slide substrates were spin dried, and were then aged at approximately 45° C. for approximately 24 hours. The slide substrates were ready for use in subsequent step.

EXAMPLE 2

Preparation of Nucleic Acid Probe Spots on Poly(L-lysine)-Coated Substrate cDNA spots were applied to a poly(L-lysine) coated surface of the substrate from Example 1 using either a pin spotter common in the art such as the SpotBot from TeleChem International, or "inkjet" spotters which are commercially available from Microfab Technologies. To accommodate densities beyond what off the shelf solutions provide customs systems can be manufactured by motivated investigators. The placement of the biomolecules and the density of the features in the resulting array is software controlled with computers. cDNA acid spots were dried and crosslinked at 450 or 1800 mJoules using a Stratalinker.

EXAMPLE 3

Treatment of Substrate Surface with Triethoxysilylpropyl Succinic Anhydride

The 3-(triethoxysilyl)propyl-succinic anhydride used in this example was purchased from (Gelest, Inc. Cat# SIT8192.6) and used as received. The substrate of Example 2 was immersed in 50 mM NaOH for approximately thirty seconds. The substrate was then immersed in a freshly made solution of 7.9 g 3-(triethoxysilyl)propyl-succinic anhydride dissolved in 139.3 mL 1-methyl-2-pyrrolidone and 10.7 mL of 1M Sodium Borate, pH 8.0 (pH approximately 8.0 per 158 mL) for approximately 30 minutes with stirring. The substrate was then washed for approximately 10 minutes in Milli-Q water, with stirring. It was then rinsed in ethanol for approximately 1 minute. After washing in the above manner, the slide substrate was dried with nitrogen gun and then baked in a convection oven in ambient air at approximately 80° centigrade for approximately 3 hours (which results in substrate shown in FIG. 4A), or approximately 17 hours (which results in FIG. 4B). Effective results were achieved with slide substrates prepared in the above manner by baking between approximately one and approximately seventeen hours at temperatures from between approximately 500 degrees centigrade and approximately 80° centigrade.

EXAMPLE 4

Exposure of Substrates to Mock Hybridization Condition

Figure 4A:
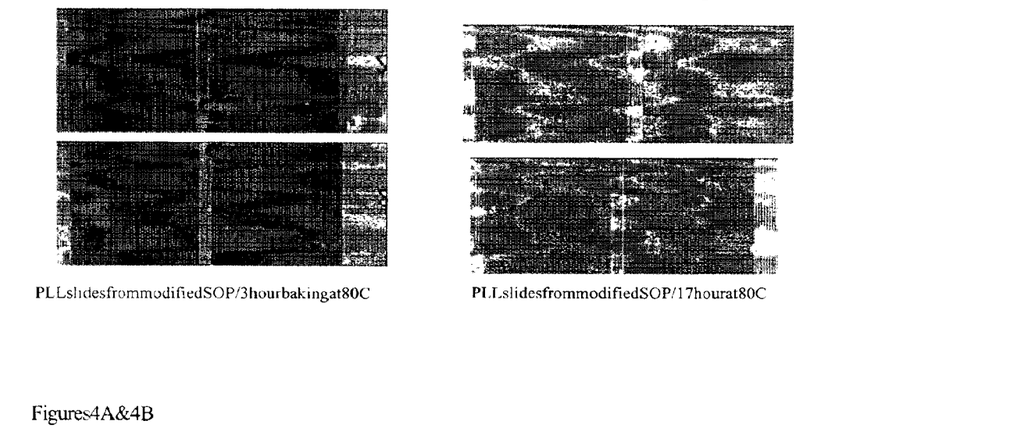

In this Example substrates prepared in accordance with the invention were exposed to "mock" hybridization conditions to evaluate microarray stability of the covalently bound polyelectrolyte layers of the invention. Substrate slides from Example 3 were each treated with both EDTA-LiMES and SSC buffers. FIG. 4A is a fluorescent image of a pair of slide substrates from Example 3 with approximately 3 hours baking at approximately 80° C., in which the left half of each slide was covered with 6 mM EDTA LiMES buffer, and the right side covered with SSC buffer, followed by baking and rotating for seventeen hours at 65° centigrade. As can be seen the poly(L-lysine) coating on the slides maintained structural integrity with no deformation or deadsorption resulting from exposure to the mock hybridization conditions and subsequent baking.

FIG. 4B is a fluorescent image of a pair of slide substrates from Example 3 with approximately 17 hours baking at approximately 80° C., in which the left half of each slide was covered with 6 mM EDTA LiMES buffer, and the right side covered with SSC buffer, followed by baking and rotating for 17 hours at 65° centigrade. Once again, the poly(L-lysine) coatings exhibited no deformation or deadsorption from exposure to the mock hybridization conditions and extended subsequent baking.

Figure 3A:
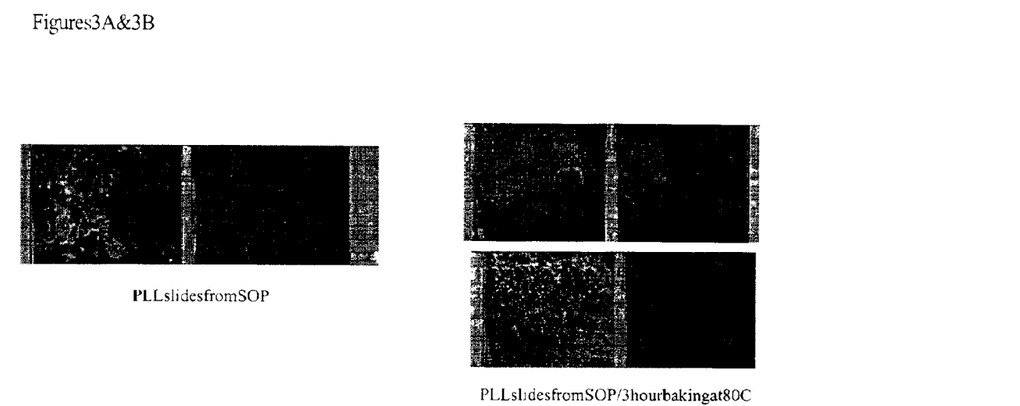

For comparison purposes, slide substrates were prepared wherein the poly(L-lysine) was treated with a conventional succinic anhydride passivating buffer, followed by rinsing and drying. The succinic anhydride, while effective for passivating free amino groups in the poly(L-lysine) layer), has no functional group for subsequent covalent bonding to the slide surface as provided by the invention. FIG. 3A is a fluorescent image of such slide with no baking after treated with succinic anhydride passivating buffer and after washing. The left and right sides of the slide were respectively covered with 6 mM EDTA LiMES and SSC buffer, and with subsequent baking for 17 hours at 65° centigrade. Regions of deadsorption can be seen, particularly in the portion of the slide treated with EDTA LiMES buffer. FIG. 3B shows fluorescent images of succinic anhydride-treated slides, with subsequent baking for 3 hours at 80° centigrade. The slide was exposed to 6 mM EDTA LiMES and SSC buffer as described above, followed by baking and rotating for seventeen hours at 65° centigrade. The regions of the slides treated with EDTA LiMES buffer show extensive deadsorption of the poly(L-lysine) from the slide surface.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for fabricating a microarray, said method comprising:
   (a) producing a polyelectrolyte layer on at least one surface of a substrate;
   (b) depositing a plurality of spots of ligands on said polyelectrolyte layer, said ligand spots arranged in an array pattern:
   (c) contacting said polyelectrolyte layer with a reagent comprising:
      (i) a passivating moiety that reacts with said polyelectrolyte layer, and
      (ii) a substrate reactive functionality; and,
   (d) producing a covalent bond between said substrate reactive functionality and said substrate wherein said substrate reactive functionality is a trialkoxysilyl anhydride.

2. The method of claim 1, further comprising cross-linking said ligand spots onto said polyelectrolyte layer.

3. The method of claim 2, wherein said ligands comprise nucleic acids.

4. The method of claim 1, wherein said depositing step (b) comprises depositing a plurality of different aqueous volumes of ligands on said polyelectrolyte layer.

5. The method according to claim 4, wherein said ligands are nucleic acids.

6. The method according to claim 4, wherein said ligands are peptides.

7. The method according to claim 4, wherein said plurality of aqueous volumes are deposited by ink-jet deposition.

8. A method for fabricating a microarray, said method comprising:
   (a) producing a polyamine layer on at least one silica surface of a substrate;
   (b) depositing a plurality of spots of ligands on said polymine layer, said ligand spots arranged in an array pattern;
   (c) contacting said polyamine layer with a solution of a trialkoxysilyl anhydride; and
   (d) forming a covalent bond between said anhydride and said polyamine layer and a covalent silicon-oxygen bond between said trialkoxysilyl propyl anhydride and said silica surface on said substrate.

9. The method of claim 8, wherein said polyamine comprises poly(L-lysine).

10. The method of claim 8, wherein said trialkoxysilyl anhydride comprises a compound having the structure;

wherein n is either zero or an integer from 1 to 10, m is either zero or an integer from 1 to 10, and R is an alkyl or functionally terminated alkenyl group.

11. The method of claim 10, wherein n is an integer equal to 1 or 2, and m is either zero or an integer from 1 to 4.

12. The method of claim 8, wherein said trialkoxysilyl anhydride comprises 3-(triethoxysilyl)propyl-succinic anhydride.

13. The method of claim 8, further comprising cross-linking said ligand spots onto said polyamine layer.

14. The method of claim 8, wherein said ligands comprise nucleic acids.

15. The method of claim 8, wherein said depositing step (b) comprises depositing a plurality of different aqueous volumes of ligands on said polyelectrolyte layer.

16. The method according to claim 15, wherein said ligands are nucleic acids.

17. The method according to claim 15, wherein said ligands are peptides.

18. The method according to claim 15, wherein said plurality of aqueous volumes are deposited by ink-jet deposition.

19. A method for fabricating a microarray, said method comprising:
   (a) producing a polyelectrolyte layer on at least one surface of a substrate;
   (b) depositing a plurality of different aqueous volumes on said polyelectrolyte layer in an array pattern to produce an array of deposited spots, wherein each aqueous volume of said plurality comprises a polymer;
   (c) contacting said polyelectrolyte layer with a reagent comprising:
      (i) a passivating moiety that reads with said polyelectrolyte layer, and
      (ii) a substrate reactive functionality; and
   (d) producing a covalent bond between said substrate reactive functionality and said substrate, wherein said substrate reactive functionality is a trialkoxysilyl anhydride.

20. The method of claim 19, further comprising cross-linking polymers of said deposited spots onto said polyelectrolyte layer.

21. The method of claim 19, wherein said polymers are nucleic acids.

22. The method of claim 19, wherein said polymers are peptides.

23. The method according to claim 19, wherein said plurality of aqueous volumes are deposited by ink-jet deposition.

24. The method according to claim 19, wherein said polyelectrolyte is a polyamine.

25. The method of claim 24, wherein said polyamine comprises poly(L-lysine).

26. The method of claim 19, wherein said reagent is a trialkoxysilyl anhydride.

27. The method of claim 26, wherein said trialkoxysilyl anhydride comprises a compound having the structure:

wherein n is either zero or an integer from 1 to 10, m is either zero or an integer from 1 to 10, and R is an alkyl or functionally terminated alkenyl group.

28. The method of claim 27, wherein n is an integer equal a 1 or 2, and m is either zero or an integer from 1 to 4.

29. The method of claim 26, wherein said trialkoxysilyl anhydride comprises 3-(triethoxysilyl)propyl-succinic anhydride.

30. A method for fabricating a nucleic acid microarray, said method comprising:
(a) producing a polyamine layer on at least one silica surface of a substrate;
(b) depositing a plurality of different aqueous volumes of nucleic acids on said polyamine layer in an array pattern to produce an array of deposited nucleic acid spots;
(c) contacting said polyamine layer with a solution of a trialkoxysilyl anhydride; and
(d) forming a covalent bond between said anhydride an said polyamine layer and a covalent silicon-oxygen bond between said trialkoxysilyl propyl anhydride and said silica surface on said substrate.

31. The method of claim 30, wherein said polyamine comprises poly(L-lysine).

32. The method of claim 30, wherein said trialkoxysilyl anhydride comprises a compound having the structure:

wherein n is either zero or an integer from 1 to 10, m is either zero or an integer from 1 to 10, and R is an alkyl or functionally terminated alkenyl group.

33. The method of claim 32, wherein n is an integer equal 1 or 2, and m is either zero or an integer from 1 to 4.

34. The method of claim 30, wherein said trialkoxysilyl anhydride comprises 3-(triethoxysilyl)proply-succinic anhydride.

35. The method of claim 30, further comprising cross-linking said nucleic acid spots onto said polyamine layer.

36. The method of claim 35, wherein said trialkoxysilyl anhydride comprises a compound having the structure:

wherein n is either zero or an integer from 1 to 10, m is either zero or an integer from 1 to 10, and R is an alkyl or functionally terminated alkenyl group.

37. The method of claim 36, wherein n is an integer equal to 1 or 2, and m is either zero or an integer from 1 to 4.

38. A method for fabricating a peptide microarray, said method comprising:
(a) producing a polyamine layer on at least one silica surface of a substrate;
(b) depositing a plurality of different aqueous volumes of peptides on said polyamine layer in an array pattern to produce an array of deposited peptide spots;
(c) contacting said polyamine layer with a solution of a trialkoxysilyl anhydride; and
(d) forming a covalent bond between said anhydride an said polyamine layer and a covalent silicon-oxygen bond between said trialkoxysilyl propyl anhydride and said silica surface on said substrate.

39. The method of claim 38, wherein said polyamine comprises poly(L-lysine).

40. The method of claim 38, wherein said trialkoxysilyl anhydride comprises 3-(triethoxysilyl)propyl-succinic anhydride.

41. The method of claim 38, further comprising cross-linking said nucleic acid spots onto said polyamine layer.

* * * * *